United States Patent
Peters

[11] 4,052,414
[45] Oct. 4, 1977

[54] CIS-ZEARALANONE, CIS-ZEARALENOL, AND CIS-ZEARALENE

[75] Inventor: Charles Allan Peters, Wichita, Kans.

[73] Assignee: IMC Chemical Group, Inc., Terre Haute, Ind.

[21] Appl. No.: 633,691

[22] Filed: Nov. 20, 1975

Related U.S. Application Data

[63] Continuation-in-part of Ser. No. 523,414, Nov. 13, 1974, abandoned, which is a continuation of Ser. No. 317,117, Dec. 21, 1972, abandoned, which is a continuation-in-part of Ser. No. 119,833, March 1, 1971, abandoned.

[51] Int. Cl.² .............................. C07D 313/00
[52] U.S. Cl. .................. 260/343.41; 424/279; 204/158 R
[58] Field of Search ................... 260/343.2 F

[56] References Cited

U.S. PATENT DOCUMENTS

| | | | |
|---|---|---|---|
| 3,535,343 | 10/1970 | Cross et al. | 260/343.2 |
| 3,551,454 | 12/1970 | Taub et al. | 260/343.2 |
| 3,551,455 | 12/1970 | Girotra et al. | 260/343.2 |
| 3,574,235 | 4/1971 | Young | 260/343.2 |
| 3,624,144 | 11/1971 | Wendler et al. | 260/343.2 |
| 3,758,511 | 9/1973 | Wendler et al. | 260/343.2 |

OTHER PUBLICATIONS

Urry et al., Tetrahedron Letters, No. 27, pp. 3109-3114 (1966).

*Primary Examiner* — John M. Ford
*Attorney, Agent, or Firm* — Bernard & Brown

[57] ABSTRACT

Cis isomers of compounds represented by the formula

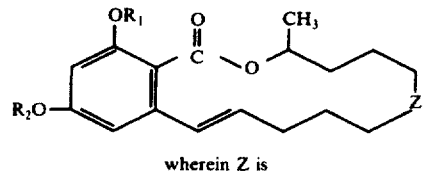

wherein Z is

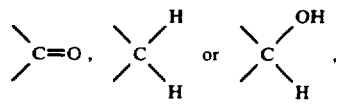

are prepared by electromagnetic irradiation (about 2800 to 3500 angstroms wavelength) of their respective trans isomers. The cis isomers of the compounds of this invention are of the class of compounds known to exhibit anabolic and estrogenic activity and may be employed as animal growth promoting agents.

6 Claims, No Drawings

CIS-ZEARALANONE, CIS-ZEARALENOL, AND CIS-ZEARALENE

The application is a continuation-in-part application of application Ser. No. 523,414, (now abandoned) filed Nov. 13, 1974, which in turn is a continuation of Serial No. 317,117, (now abandoned) filed Dec. 21, 1972, which in turn is a continuation-in-part of Ser. No. 119,833, (now abandoned) filed Mar. 1, 1971.

This invention relates to a process of making cis isomers of compounds represented by the formula

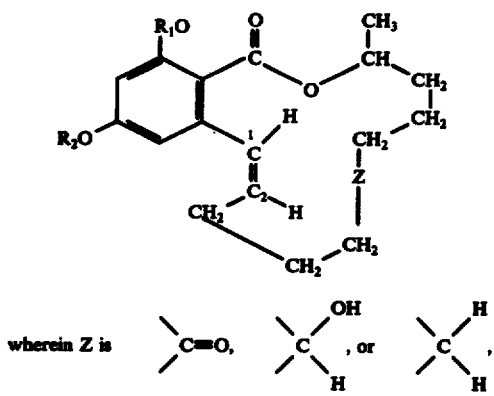

and each of $R_1$ and $R_2$ can be hydrogen; alkyl (substituted or unsubstituted), e.g., containing 1 to about 15 carbon atoms, such as lower alkyl, e.g., methyl, ethyl, hexyl, etc., and including cyclohexyl, etc.; alkanoyl, e.g., containing about 2 to 25 carbon atoms, such as lower alkanoyl, e.g., acetyl, valeryl, propionyl, etc; aryl (including alkaryl and aralkyl), e.g., containing up to about 20 carbon atoms, for instance containing up to about 10 aromatic carbon atoms and up to about 10 alkyl carbon atoms (for example as lower alkyl groups having, say, 1 to 6 carbon atoms), e.g. monocyclic aryl such as benzyl, bromobenzyl, and the like. These compounds are advantageously produced from their respective trans isomers by irradiation with electromagnetic radiation having a wavelength of about 2800 to 3500 angstroms. The cis compounds of this invention can be produced essentially pure, e.g., generally above 90 weight percent, often above about 97 percent pure. This invention also relates to the use of cis isomers of zearalenone and its derivatives as animal growth promoters.

The conversion of trans-zearalenone and trans-zearalenol to their corresponding cis isomers by a photochemical process is disclosed in Belgian Pat. No. 776,194, issued Dec. 31, 1971. The Belgian patent corresponds to U.S. patent application Ser. No. 119,833, (now abandoned) filed Mar. 1, 1971.

The compounds prepared in accordance with this invention include cis-zearalenone (also known as 6-(10-hydroxy-6-oxo-cis-undecenyl)-β-resorcylic acid-μlactone) and derivatives thereof. Because of the ethylenic unsaturation between the 1 and 2 position carbon atoms in the lactone ring of such, as in zearalenone, the compounds can theoretically exist in two stereoisomeric forms: cis and trans. The zearalenone produced by cultivation of the microoganism *Gibberella zeae* on a suitable nutrient, as described, for example, in U.S. Pat. No. 3,196,019 to Andrews et al., has been in the trans form. Zearalenone is anabolically and estrogenically active and useful as an animal growth promoter.

The compound zearalenol (also known as 6-(6,10-dihydroxy-trans-undecenyl)-β-resorcylic acid-μ-lactone) exhibits anabolic and estrogenic activity and is useful, for example, when administered as an implant to animals to promote growth. Zearalenol may be prepared by reduction of the keto group of zearalenone to an alcohol group. This reaction is described, for example, in U.S. Pat. No. 3,239,348 to Hodge et al. The compound zearalene (also known as 6-(10-hydroxy-trans-1-undecenyl)-β-resorcylic acid-μ-lactone) exhibits estrogenic activity and aids in increasing the rate of growth in meat producing animals. Zearalene may be prepared by the reduction of the keto group of zearalenone to replace the oxygen of the keto group with two hydrogen atoms. This reaction is described, for example, in U.S. patent application No. 561,898 of Kavka, filed Mar. 25, 1975, which is a continuation of Application Ser. No. 476,888, filed June 6, 1974.

One or both of the hydroxy substituents on the benzene ring of zearalenone, zearalenol, or zearalene may undergo replacement of the hydrogen atom with an alkyl, alkanoyl, aryl, or aralkyl radical. Conventional processes for the hydrogen replacement reaction may be employed and are illustrated, for instance, in U.S. Pat. Nos. 3,239,341; 3,239,342; 3,239,347; 3,239,348; and 3,373,039 to Hodge et al.

It is realized, for instance, that cis-zearalenol or cis-zearalene may be prepared by the appropriate reduction of the keto group in cis-zearalenone to an alcohol group or hydrogens. Similarly, the hydrogen atoms of the hydroxy groups on the benzene ring of a cis compound may be replaced to provide the desired cis-derivative.

Identification of the cis isomers can be by nuclear magnetic resonance spectroscopy (nmr). For instance, whereas the proton on the 1 position lactone ring carbon atom in trans-zearalenone exhibits an absorption at 7.14δ, in cis-zearalenone it exhibits an absorpiton at only 6.72δ. The coupling constant, J, between the hydrogen atoms located on 1 and 2 position lactone ring carbon atoms is 16 Hz in the trans isomer and only 11.5 Hz in the cis isomer. As regards to zearalenol and zearalene, similar differences in the nmr absorption of the protons on the 1 and 2 position lactone ring carbon atoms are found between the cis and trans isomers.

In addition, a comparison of the nmr spectra of trans-zearalenone and cis-zearalenone shows that a number of other protons in the molecule undergo shielding effects due to the change in molecular shape when trans-zearalenone is irradiated according to the process of the present invention. For example, the signal for the proton on the 5 position carbon atom of the aromatic ring is shifted upfield by 18 Hz due to a shielding effect by the carbon-carbon double bond. Other upfield shifts by the allylic protons on the 3 position lactone ring carbon and the protons on the 5 and 7 position lactone ring carbons are probably due to the shielding effect by the aromatic π-electrons as a result of the fourteen-member ring being folded over the shielding cone of the aromatic ring. Similar shielding effects are observed for cis-zearalenol and other cis-derivatives of zearalenone.

As a point of information, the compounds of the process of this invention wherein Z is

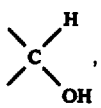

zearalenol for instance, whether in cis or trans form, can also, and do, exist in two different diasterioisomeric arrangements based on the substitutions on the 6 position carbon atom, i.e., the hydroxylated carbon atom, in the lactone ring. For example, when the compound is trans-zearalenol, one diastereoisomer, or diamer, has a melting point of about 167°–168° C., the other a melting point of about 174°–176° C.

The irradiation of the trans isomers to produce the cis-isomers of the invention can be carried out with an ultraviolet irradiation source which can produce a wavelength generally in the range of about 2800 to 3500 angstroms. The irradiation dosages in these wavelengths may often be at least about 10 kwh./hr./kg. of starting material, preferably about 20 to 500 kwh./hr./kg. of starting material. The length of time that the trans isomer is exposed to the irradiation can vary widely depending upon such factors as the amount of trans isomer, the irradiation wavelength, dosage, etc. Generally, the irradiation is continued for a period of about 1 to 200 or more hours and preferably for a period of about 6 to 120 hours.

Typical sources of ultraviolet irradiation which can be used in the present process include mercury vapor lamps, carbon arc lamps, and tungsten arc lamps.

The irradiation is preferably effected with the trans isomers in solution in a stable solvent, i.e., one which is non-reactive with the starting material and product under the irradiation conditions. Suitable solvents include lower monohydric alkanols, acetonitrile, and dichloromethane. Methanol is preferred. Preferred solution concentrations are about 0.5 to 2.5, most preferably about 1 to 2, weight percent.

It is also preferred that the trans isomer be essentially free from contact with oxygen during the irradiation, the reason being that oxygen might possibly inhibit the stereoisomerization and/or oxidize the reactants. Where solution irradiation is employed this can be achieved, for example, by first purging the solution with an inert gas such as nitrogen, argon or helium and then maintaining the solution in an atmosphere of inert gas during the irradiation.

The maximum amount of cis isomer that can be obtained in the product of the photochemical process of this invention is generally about 90 percent, e.g., approximately 97 percent. In the case of zearalenone, approximately two-thirds of the isomerized trans isomer can be removed from the crude product mixture via recrystallization, yielding a 99% cis-zearalenone product. Suitable solvent systems for the recrystallization include lower monohydric alkanol/water mixtures such as methanol/water mixtures and isopropanol/water mixtures. Most preferred is a methanol/water mixture containing about 20 to 50 volume percent water.

The crude cis-zearalenol product can be upgraded by column chromatography using a column packing such as silicic acid or alumina. The crude cis-zearalene product may conveniently be recrystallized from benzene to upgrade purity. It is generally advantageous to treat product solutions of cis isomers with activated charcoal so as to enhance the purity of the product.

The irradiation is preferably continued until the cis-/trans isomeric mixture contains at least about 90 percent, or even at least about 95 percent, of the cis isomer.

Slightly elevated, room, or lowered temperatures (e.g., about 15°–45° C.) and superatmospheric, atmospheric, or subatmospheric pressures can be used for the stereoisomerization reaction of the present invention. For reasons of economy, however, it is preferred to operate under ambient conditions, i.e., at room temperature and atmospheric pressure. It should be realized that the process of this invention may be employed to convert both the R and S conformers of trans-zearalenone or a derivative thereof to the corresponding cis isomer.

The alternative method of producing cis-zearalenol or derivative thereof, by reducing the ketone group of cis-zearalenone or a corresponding cis-zearalenone derivative, is conducted under cis-zearalenone reducing conditions of temperature and pressure in the presence of a suitable reducing agent and is also preferably carried out with the cis-zearalenone in solution in a stable solvent, e.g., dimethylformamide, tetrahydrofuran, or a lower monohydric alkanol, such as isopropanol, methanol or ethanol. Preferred solution concentrations are about 5 to 10 weight percent.

Any reducing agent which is selective for the ketone group of the cis-zearalenone and unreactive with the solvent can be employed in the reaction. Most preferred is a borohydride such as sodium borohydride and potassium borohydride. The latter should not be used, however, in conjunction with an alcohol solvent. These borohydride reducing agents are advantageously employed in an amount which is at least equimolar to the amount of cis-zearalenone.

Subatmospheric, atmospheric, or superatmospheric pressures can be used for the reduction reaction, with atmospheric pressure being preferred for economic reasons. The temperature to be employed will depend upon the choice of reducing agent and solvent, but will generally be about 15° to 45° C.

The alternative method of producing cis-zearalene or derivative thereof is by the reduction of the ketone group of cis-zearalenone or corresponding derivative of cis-zearalenone, to replace the oxygen of the ketone group with two hydrogen atoms. The reduction of the ketone group can best be effected by treating the cis-zearalenone type compound with zinc and hydrogen chloride, while dissolved in acetic anhydride.

Cis-compounds wherein the substituents on the benzene ring are hydroxyl groups may be converted to compounds in which one or both of $R_1$ and $R_2$ are alkyl, alkanoyl, aryl, or aralkyl. In producing the compounds of the present invention where R is alkyl, conventional alkylation procedures may be used to replace the hydrogen atom of one or both of the hydroxyl groups on the benzene ring with an alkyl group. The alkylation may be by reaction with the corresponding dialkyl sulfates, e.g., dimethyl sulfate, diethyl sulfate, etc., to produce a dialkyl substituted compound or a monoalkyl substituted compound with the alkyl group replacing the hydrogen of the hydroxyl group ortho to the ester group. The alkylation reaction may take place in a liquid medium such as water. Furthermore, a methyl group may selectively replace the hydrogen of the hydroxyl group para to the ester group on the benzene ring by using diazomethane.

The hydrogen atoms of the hydroxyl substituents on the benzene ring may be replaced by a carbon-containing, cyclic group by a condensation reaction in a slightly alkaline organic solvent medium with the corresponding acid anhydride or chloride of the cyclic compound. Illustrative of cyclic substituents, alkyl and aryl or aralkyl, are benzyl, bromobenzyl, benzothiazolyl, phenyltetrazolyl, benzoxazolyl, tetrahydrofuranyl, tetrahydropyranyl, cyclopentyl, cyclohexyl, naphthyl, etc.

Where R is desired to be alkanoyl, conventional acylation procedures may be used to replace one or both of the hydrogen atoms of the hydroxyl groups on the benzene nucleus with alkanoly radicals. For instance, acylation may be effected by reaction with the corresponding acid anhydride, e.g., acetic anhydride, propionic anhydride, etc., catalyzed with, for example, sodium acetate or phyridine. Ambient conditions may be employed, although it is preferred to keep the reaction mixture cold.

The cis isomers of the present invention can be administered to animals by any suitable method, including oral and parenteral administrations or as an implant. For example, the compounds can be blended with ordinary feed which contains nutritional values in an amount sufficient to produce the desired rate of growth and thus be fed directly to the animals, or the compounds can be suspended in a suitable injection suspension medium, such as peanut oil, and injected parenterally. The amount of compound fed to an animal varies, of course, upon the animal, the desired rate of growth, and the like. In general, from 2.5 to 50 grams of the compound per ton of feed is typical. When an implant is used, for example a ball or cylindrical implant inserted under the skin on the ear of an animal, e.g., a lamb or steer, the implant will generally contain from 1 mg. to 100 mg. of the compound.

When an isomer of this invention is to be administered to animals in their feed, an animal feed composition may be prepared containing the usual nutritionally-balanced quantities of carbohydrates, proteins, vitamins, and minerals together with the isomer. Some of the usual sources of these dietary elements are grains, such as ground grain and grain by-products; animal protein substances, such as those found in fish meal and meat scraps vegetable proteins, such as soybean oil meal or peanut oil meal; vitaminaceous materials, e.g., vitamins A and D mixtures; riboflavin supplements and other vitamin B complex members; and bone meal and limestone to provide minerals. A type of conventional feed material for use with cattle, for example, includes alfalfa hay and ground corn cobs, together with supplementary vitaminaceous substances if desired.

EXAMPLE I

This example illustrates the preparation of cis-zearalenone.

Three grams of trans-zearalenone is dissolved in 500 ml. of methanol and the solution is placed in a 500 ml. photochemical reactor (Ace Glass Model 6515) equipped with a borosilicate glass immersion well (Ace Glass Model 6517-05). The solution is purged overnight (about 12 hours) with nitrogen and is then irradiated under nitrogen atmosphere with a 450 watt, medium pressure, mercury vapor lamp (Ace Glass Model 6515-34) for 41 hours. The resulting solution is slurried with one gram of charcoal ("KB"), filtered, and the filtrate evaporated to dryness under vacuum on a rotary evaporator to give 2.98 grams of a very pale yellow solid. The latter is recrystallized twice from a mixture of 25 ml. of methanol and 15 ml. of water to give 2.2 grams (representing a 73.5% yield) of white crystals which are identified by nmr as about 99% cis-zearalenone. The crystals melt at 133°-134.5° C. and analyze as 68.19 weight percent carbon and 7.23 weight percent hydrogen, as compared with theoretical values of 67.92 percent carbon and 6.92 percent hydrogen.

EXAMPLE II

The procedure of Example I, above, is repeated using a solution of 10 grams of trans-zearalenone in 500 ml. of methanol and an irradiation time of 72 to 96 hours. The crude product amounts to 9.9 grams. The recrystallized cis-zearalenone weighs 8.8 grams (representing an 88% yield) and melts at 134°-135° C.

EXAMPLE III

This example illustrates the preparation of cis-zearalenol from the higher melting diamer of trans-zearalenol.

Ten grams of the higher melting diamer of trans-zearalenol is dissolved in 500 ml. of methanol and the solution is placed in a 500 ml. photochemical reactor (Ace Glass Model 6515) equipped with a borosilicate glass immersion well (Ace Glass Model 6517-05). The solution is purged overnight (about 12 hours) with nitrogen and is then irradiated under nitrogen atmosphere with a 450 watt, medium pressure, mercury vapor lamp (Ace Glass Model 6515-34) for 91 hours. The resulting light yellow solution is slurried with one gram of charcoal ("KB"), filtered, and the filtrate evaporated to dryness under vacuum on a rotary evaporator to give 9.42 grams of a light yellow solid. The latter is redissolved in a minimum amount of a mixture of 3 weight percent methanol and 97 weight percent chloroform, the resultant solution placed on a 5 centimeter diameter column of silicic acid ("SilicAR CC-7", 200 grams), and the column then eluted with an additional portion of the methanol/chloroform mixture. Evaporation to dryness of the eluate yields 8.1 grams of a white solid identified by nmr to be about 97% cis-zearalenol. The solid melts at about 132°-134° C. and analyzes as 67.38 weight percent carbon and 7.62 weight percent hydrogen, as compared with theoretical values of 67.50% carbon and 7.50 hydrogen.

EXAMPLE IV

This example illustrates the preparation of cis-zearalenol from the lower melting diamer of trans-zearalenol.

Five grams of the lower melting diamer of trans-zearalenol is dissolved in 500 ml. of methanol and the solution is placed in a 500 ml. photochemical reactor (Ace Glass Model 6515) equipped with a borosilicate glass immersion well (Ace Glass Model 6517-05). The solution is purged overnight (about 12 hours) with nitrogen and is then irradiated under nitrogen atmosphere with a 450 watt, medium pressure, mercury vapor lamp (Ace Glass Model 6515-34) for 48 hours. The resulting solution is slurried with one gram of charcoal ("KB"), filtered, and the filtrate evaporated to dryness under vacuum on a rotary evaporator to give 4.65 grams of a light yellow solid. The latter is purified by the column chromatography method of Example III, above, to yield 4.3 grams of a white solid identified by nmr to be about 97% cis-zearalenol. The solid melts at about 125°-128° C. and analyzes as 67.51 weight percent carbon and 7.53 weight percent hydrogen, as compared with theoretical values of 67.50% carbon and 7.50% hydrogen.

EXAMPLE V

This example illustrates the preparation of cis-zearalenol from cis-zearalenone.

Sodium borohydride (1 gram) is slowly added to 50 milliliters of methanol and 0.3 gram of cis-zearalenone while cooling the resultant reaction mixture. The mixture is then heated for 2 hours on a steam bath to evaporate the methanol. The residue is neutralized with HCl and extracted with two 40 milliliter portions of chloroform. The chloroform is then evaporated and the residue is purified by the column chromatography procedure of Example III, above, to yield about 0.28 gram of mixed diamers of cis-zearalenol.

EXAMPLE VI

This example illustrates the estrogenic activities of cis-zearalenone and cis-zearalenol.

Samples of cis-zearalenone and cis-zearalenol are tested for uterotropic activity according to the well known mouse uterine test. This test consists of feeding the test material in admixture with a standard feed to eight, adult, ovariectomized female mice at a ration of 3 grams per day for a five-day period. On day six the animals are weighed and sacrificed, and their uteri removed and weighed. Estrogenic activity is confirmed if the uterus of the test mouse is heavier and accounts for a greater percentage of the mouse's body weight than the uterus of a control mouse. Test results are reported in Table I, as are, for comparison purposes, the test results on trans-zearalenone and trans-zearalenol. Each cis isomer tested is compared to a sample of trans isomer taken from the same batch as that from which the cis isomer was prepared.

TABLE I

| Test Compound | Daily Dose (mcg/g feed) | Uterine Wt. (mg.) | % Body Wt. |
|---|---|---|---|
| Control | — | 11.5 | 0.049 |
| Trans-zearalenone | 25 | 28.2 | 0.114 |
| 99% cis-zearalenone | 25 | 25.7 | 0.107 |
| Trans-zearalenol higher melting diamer | 50 | 11.2 | 0.050 |
| 97% cis-zearalenol from higher melting diamer of trans-zearalenol | 50 | 32.1 | 0.139 |
| 97% cis-zearalenol from higher melting diamer of trans-zearalenol | 100 | 51.8 | 0.226 |
| Trans-zearalenol lower melting diamer | 6.25 | 19.1 | 0.079 |
| 97% cis-zearalenol from lower melting diamer of trans-zearalenol | 3.125 | 32.2 | 0.133 |
| 97% cis-zearalenol from lower melting diamer of trans-zearalenol | 6.25 | 49.3 | 0.208 |

The above data also show that the cis isomers of the zearalenols, surprisingly, further demonstrate substantially more activity than their respective trans isomers.

EXAMPLE VII

This example illustrates the use of cis-zearalenol as a growth promoting supplement in animal feed.

Six head of cattle are fed a daily ration of a mixture of alfalfa hay and ground corn cobs that has been supplemented with 10 ounces of 97% cis-zearalenol prepared as in Example III, above, for each one hundred pounds of mixture.

EXAMPLE VIII

This example illustrates the use of cis-zearalenone as a growth promoting supplement in animal feed.

Six head of swine are fed a daily ration of a mixture of alfalfa hay and ground corn cobs that has been supplemented with 10 hounces of 99% cis-zearalenone that has been prepared as in Example II, above, for each one hundred pounds of mixture.

EXAMPLE IX

This example illustrates the use of cis-zearalenol as a growth promoting agent when used as an implant on lambs.

Forty, four-month old lambs are each implanted subcutaneously at the base of an ear with a cylindrical implant. The implant is 0.090 inch diameter and 0.130 inch long. The implant weighs 16 milligrams and contains a pharmaceutically acceptable carrier and 12 milligrams of the 97% cis-zearalenol prepared as in Example III above.

EXAMPLE X

This example illustrates the use of cis-zearalenol as a growth promoting agent when used as an implant on steers.

Ten, ten-month old steers are each implanted subcutaneously at the base of an ear with a one-eighth inch diameter spherical implant. The implant weighs 19 milligrams and contains a pharmaceutically acceptable carrier and 12 milligrams of the 97% cis-zearalenol prepared as in Example IV above.

EXAMPLE XI

This example illustrates the preparation of cis-zearalene from trans-zearalene in accordance with the method of this invention. One gram of trans-zearalene is dissolved in 500 milliliters of methanol, and the solution is placed in a 500 milliliter photochemical reactor (Ace Glass Model 6515) equipped with a borosilicate glass immersion well (Ace Glass Model 6517-05). The solution is purged with nitrogen for about 12 hours and is then irradiated under a nitrogen atmosphere with a 450-watt, medium pressure, mercury vapor lamp (Ace Glass Model 6515-34) for 24 hours. The resulting solution is evaporated to dryness under vacuum on a rotary evaporater and the residue is recrystallized from benzene to give 0.70 gram of cis-zearalene as white crystals having a melting point of 143° to 145° C. Analysis indicated the presence of 70.67 weight percent carbon and 8.27 weight percent hydrogen, as compared with theoretical values of 71.05 weight percent carbon and 7.89 weight percent hydrogen.

EXAMPLE XII

Samples of cis-zearalene are tested for uterotropic activity according to the well known mouse uterine test. This test consists of feeding the test compound in a sesame oil carrier to ten, adult, ovariectomized female mice for three days at a ration of 50, 100, and 300 micrograms of compound per mouse per day. On day four the animals are sacrificed, and the uteri are removed and weighed. The test results are reported in Table II.

TABLE II

| Test Compound | Total Dose (mcg) | Uterine Weight (mg) | % Body Weight |
|---|---|---|---|
| Control | — | 10.3 | 0.041 |
| Trans-zearalenone | 300 | 26.2 | 0.100 |
| Trans-zearalene | 300 | 16.2 | 0.066 |
| | 900 | 18.1 | 0.070 |
| Cis-zearalene | 150 | 22.6 | 0.087 |
| | 300 | 30.3 | 0.120 |
| | 900 | 48.6 | 0.188 |

EXAMPLES XIII to XX

Essentially the same procedure used in Example I is followed to prepare cis isomers of compounds of the general formula

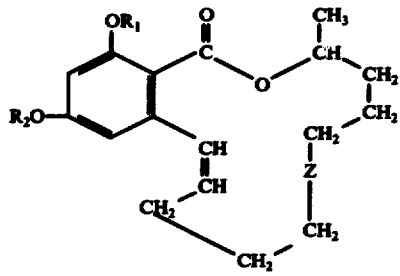

wherein the values for $R_1$, $R_2$ and Z are set forth below for the respective examples from the corresponding trans isomers wherein the values for $R_1$, $R_2$ and Z are the same as in the product. The starting compounds can be produced in accordance with the above-identified United States Patents issued to Hodge.

| EXAMPLE | $R_1$ | $R_2$ | Z |
|---|---|---|---|
| XIII | —$CH_3$ | —$CH_3$ | $\diagdown$C$H_2\diagup$ |
| XIV | —$CH_2CH_3$ | —$CH_2CH_3$ | $\diagdown$C$H_2\diagup$ |
| XV | —$\overset{\overset{O}{\|}}{C}$—$CH_3$ | —$CH_3$ | $\diagdown$C$H_2\diagup$ |
| XVI | —$CH_3$ | —$CH_3$ | $\diagdown$CHOH$\diagup$ |
| XVII | —H | benzyl | $\diagdown$C=O$\diagup$ |
| XVIII | —H | bromobenzyl | $\diagdown$C=O$\diagup$ |
| XIX | —$CH_3$ | —$\overset{\overset{O}{\|}}{C}$—$CH_3$ | $\diagdown$C$H_2\diagup$ |
| XX | —$\overset{\overset{O}{\|}}{C}$—$C_4H_9$ | —$\overset{\overset{O}{\|}}{C}$—$C_4H_9$ | $\diagdown$C=O$\diagup$ |

A feed mixture is prepared from each of the above compounds having 10 ounces of the cis isomer per one hundred pounds of mixture comprising alfalfa hay and ground corn cobs and is used to feed in daily ration portions six head of cattle.

I claim:
1. An essentially pure cis compound of the formula:

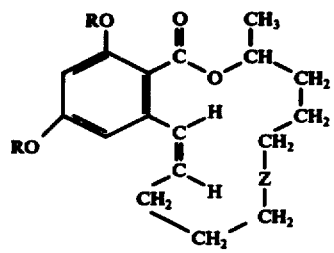

wherein Z is

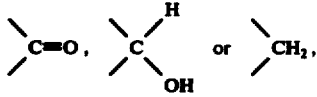

and wherein R is selected from the group consisting of hydrogen, lower alkyl, lower alkanoyl, monocyclic aryl of up to about 10 carbon atoms, and aralkyl of monocyclic aryl containing up to about 10 carbon atoms and lower alkyl.

2. Essentially pure cis-zearalenone.
3. Essentially pure cis-zearalenol.
4. The diastereoisomer of the compound of claim 3 which has the same arrangement of substituents on the 6 position carbon atom in the lactone ring as does the lower melting diastereoisomer of trans-zearalenol.
5. The diastereoisomer of the compound of claim 3 which has the same arrangement of substituents on the 6 position carbon atom in the lactone ring as does the higher melting diastereoisomer of trans-zearalenol.
6. Essentially pure cis-zearalene.

* * * * *